US012599500B2

(12) United States Patent
Peiretti et al.

(10) Patent No.: US 12,599,500 B2
(45) Date of Patent: Apr. 14, 2026

(54) OPHTHALMOLOGICAL SURGICAL INSTRUMENT

(71) Applicant: UNIVERSITA' DEGLI STUDI DI CAGLIARI, Cagliari (IT)

(72) Inventors: Enrico Peiretti, Cagliari (IT); Claudio Iovino, Cagliari (IT); Emanuele Siotto Pintor, Cagliari (IT); Pasquale Buonadonna, Cagliari (IT)

(73) Assignee: UNIVERSITA' DEGLI STUDI DI CAGLIARI (IT)

( * ) Notice: Subject to any disclaimer, the term of this patent is extended or adjusted under 35 U.S.C. 154(b) by 254 days.

(21) Appl. No.: 18/562,512

(22) PCT Filed: May 19, 2022

(86) PCT No.: PCT/IB2022/054678
§ 371 (c)(1),
(2) Date: Nov. 20, 2023

(87) PCT Pub. No.: WO2022/243929
PCT Pub. Date: Nov. 24, 2022

(65) Prior Publication Data
US 2024/0238121 A1     Jul. 18, 2024

(30) Foreign Application Priority Data

May 20, 2021     (IT) ........................ 102021000013205

(51) Int. Cl.
*A61F 9/007*          (2006.01)
*A61B 17/00*          (2006.01)
*A61B 17/3209*        (2006.01)

(52) U.S. Cl.
CPC .................... *A61F 9/00754* (2013.01); *A61B 2017/00424* (2013.01); *A61B 2017/00862* (2013.01); *A61B 17/3209* (2013.01)

(58) Field of Classification Search
CPC .. A61F 9/007; A61F 9/00736; A61F 9/00754; A61F 9/00763; A61B 17/3209; A61B 2017/2926
See application file for complete search history.

(56) References Cited

U.S. PATENT DOCUMENTS 5,860,994 A * 1/1999 Yaacobi .............. A61F 9/00754
                                                      606/166
6,165,190 A   12/2000 Nguyen
(Continued)

FOREIGN PATENT DOCUMENTS

KR   20210058629 A * 5/2021 ......... A61F 9/00736
WO        WO932076 A1  10/1993
(Continued)

OTHER PUBLICATIONS

English Machine Translation of KR20210058629A (Nam Dong Heun) from Patentscope website <hhtps:patentscope.wipo.int>. Accessed Sep. 23, 2025. (Year: 2021).*
(Continued)

*Primary Examiner* — Diane D Yabut
*Assistant Examiner* — Christian D. Knauss
(74) *Attorney, Agent, or Firm* — Widerman Malek, PL; Mark Malek

(57)          ABSTRACT

An ophthalmological surgical instrument may include a hollow body having an oblong shape, and a cutting assembly. The cutting assembly may include at least one arm and at least one cutting element. The at least one arm may be pivotally hinged on a base that may be stabilized to the body and adapted to be placed in rotatable cooperation with a toothed rack. The toothed rack may be slidingly positionable with respect to the base and adapted to engage with at least one pinion gear. The at least one pinion gear is positioned along an axis of rotation and integral with the at least one
(Continued)

arm. The rack is adapted to be manually and slidingly operated by a user.

14 Claims, 6 Drawing Sheets

(56)                    References Cited

U.S. PATENT DOCUMENTS

| | | | |
|---|---|---|---|
| 8,685,051 B2 | 4/2014 | Glazer et al. | |
| 2013/0274755 A1 * | 10/2013 | Van Dalen | A61F 9/00754 |
| | | | 606/107 |
| 2019/0183681 A1 | 6/2019 | Schaller et al. | |

FOREIGN PATENT DOCUMENTS

| | | | | |
|---|---|---|---|---|
| WO | WO-2018132299 A1 * | 7/2018 | | B26B 9/00 |
| WO | WO2020099192 A1 | 5/2020 | | |

OTHER PUBLICATIONS

WO9320765A1 published Oct. 28, 1993. WO2020099192A1 published May 20, 2020.

* cited by examiner

1

OPHTHALMOLOGICAL SURGICAL INSTRUMENT

RELATED APPLICATIONS

This application is a national phase application of and claims priority under 35 U.S.C. § 371 of PCT Application Serial No. PCT/IB2022/054678 filed on May 19, 2022 and titled OPHTHALMOLOGICAL SURGICAL INSTRU-MENT, which, in turn, claims priority under Patent Coop-eration Treaty Article 8 of Italian Patent Application No. 102021000013205 filed on May 20, 2021 and titled OPH-THALMOLOGICAL SURGICAL INSTRUMENT. The content of these applications are incorporated herein by reference except to the extent that content therein conflicts with the content herein.

TECHNICAL FIELD

The present invention relates to an ophthalmological surgical instrument.

More specifically, the present invention relates to a new ophthalmological medical-surgical instrument for perform-ing capsulorhexis phase in the surgical treatment of cata-racts.

State of the Prior Art

Surgical techniques for the treatment of human and ani-mal eye diseases, including those for the surgical treatment of cataract, are widely known in ophthalmological medicine. These types of surgical techniques can be performed manu-ally by a surgeon with traditional surgical instruments or with the help of modem medical equipment for surgical treatment with laser radiation.

Cataract is a degenerative eye disease that can occur as a result of various factors and leads, in the affected patient, to progressive opacification of the crystalline lens and a con-sequent blurring of vision up to the blindness. Cataract is a disease that affects a large part of the population in old age and can only be conclusively treated by surgery.

The treatment of cataract, regardless of the type of medi-cal technology used, essentially consists of surgical removal of the opacified crystalline lens of the human eye, but also of the animal eye in veterinary medical treatments. In order to reach the opacified crystalline lens to be removed, it is necessary to preliminarily make some small incisions, or lateral service accesses into the corneal tissue, and an access called corneal tunnel to allow the instrument access into the anterior chamber of the eye, through the corneal tissue, to the anterior surface of the capsule containing the crystalline lens for the capsulorhexis phase, so that the opacified crystalline lens can be exposed, fragmented and removed by traditional phacoemulsification surgical techniques.

The capsulorhexis phase, i.e. the operation to open the anterior capsule that allows access to the crystalline lens, through the anterior chamber, is a particularly delicate operation because it involves a small and thin portion of ocular tissue and must be performed by the surgeon with extreme precision and no margin for error.

In surgical treatment of cataract with traditional instru-ments, without laser devices, the capsulorhexis phase is carried out entirely by the manual skills of the surgeon by means of traditional special forceps.

A typical example of these well-known types of forceps in use in ophthalmic surgery is described in the document US D 341.886 (S).

In the automated surgical treatment of cataract, by means of well-known medical apparatuses such as femtosecond laser devices, the capsulorhexis phase is carried out, under the supervision of the surgeon, by a computerized electronic device that guides the laser beam during the incision of the anterior capsule tissue.

These types of known automated medical instruments and devices, however, have limitations and drawbacks in their use.

A major limitation of modern automated medical devices for laser treatment of eye diseases, including cataract, is the economic cost that could amount in an order of hundreds of thousands of euro.

Said automated medical devices are also very complex, bulky, and require periodic and constant maintenance and calibration, they can therefore generally be available only in large specialized facilities or large hospital centres.

A limitation, on the other hand, of traditional manual surgical instruments such as forceps is due to the fact that they require a high degree of manual dexterity and skill on the part of the surgeon, especially during the capsulorhexis phase, and they can therefore only be easily used almost exclusively by experienced and specialized surgeons.

OBJECT OF THE INVENTION

The purpose of the present invention is to overcome and obviate, at least in part, the above-mentioned drawbacks and limitations of the known art.

More particularly, the object of the present invention is to provide a simple ophthalmological surgical instrument such that it can be easily used even by inexperienced and unskilled surgeons.

Further object of the present invention is to provide ergonomic ophthalmological surgical instrument that is easy to handle and compact in size.

Not least object of the present invention is to provide ophthalmological surgical instrument that can also be used in the medical-veterinary field.

Another further object of the present invention is to provide an ophthalmological surgical instrument capable of ensuring a high level of durability and reliability over time, such that it can be easily and economically realized.

These and other objects are achieved by the ophthalmo-logical surgical instrument subject matter of the present invention in accordance with the independent claim.

The structural and functional features of the ophthalmo-logical surgical instrument itself may be better understood from the detailed description that follows, in which refer-ence is made to the attached drawings which represent a preferred and non-limiting embodiment where:

BRIEF DESCRIPTION OF THE FIGURES

FIG. 1a is a schematic representation of an axonometric perspective view of a preferred embodiment of the ophthal-mological surgical instrument, subject matter of the present invention;

FIG. 1b is a partial schematic representation of a detail view of FIG. 1a;

FIG. 2a is a schematic representation of a further axono-metric perspective view from another angle of view of the preferred embodiment of the same ophthalmological surgi-cal instrument subject matter of the present invention;

FIG. 2b is a partial schematic representation of a detail view of FIG. 2a;

DETAILED DESCRIPTION OF THE INVENTION

Figures 1A, 1B:
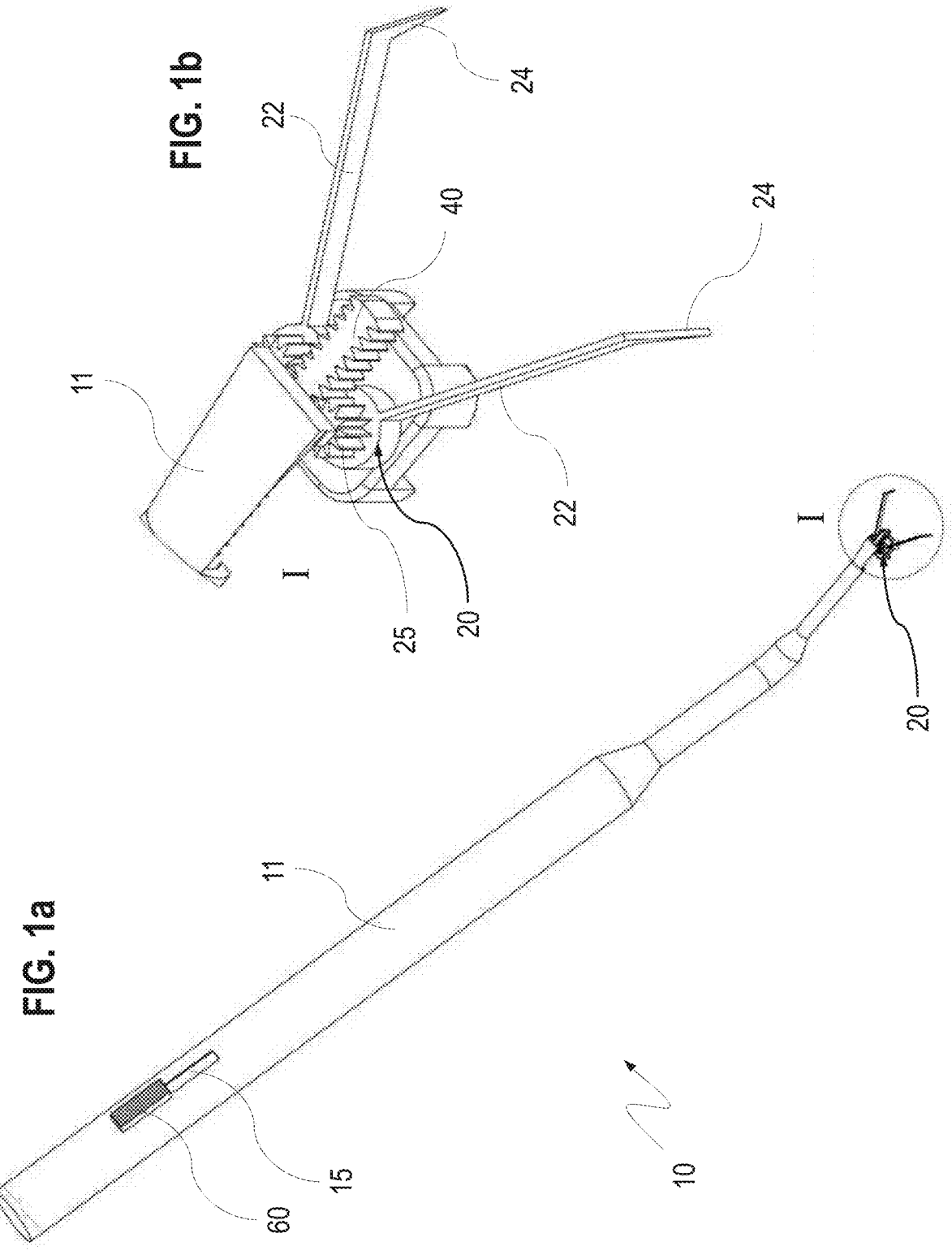

With initial reference to FIGS. 1*a* to 3*b*, there follows described in a preferred embodiment, given for illustrative and non-limiting purposes, the ophthalmological surgical instrument 10 subject matter of the present invention.

The ophthalmological surgical instrument 10 comprises:
- a hollow body 11 having an oblong shape having a substantially cylindrical or polygonal cross-section with a portion adapted to function as a handle;
- a cutting assembly 20 arranged on the opposite end of said body 11 and comprising at least one arm 22 connected to said body and provided at its free end with at least one cutting element 24.

Said surgical instrument 10 discloses the innovative features of comprising at least one arm 22 pivotally hinged on a base 30 fixed to said body 11 and configured to be rotatively placed in cooperation with a liner rack 40 slidingly arranged with respect to said base 30 and configured to kinematically engage with at least a conjugate pinion gear 25 arranged along the rotation axis and integral with said at least one arm 22, said rack 40 being suitable to be manually and slidingly operated by the user.

With particular reference to FIGS. 4*a* to 4*d*, said rack 40 is configured such that in response to an axial sliding thereof corresponds an angular movement of said at least one arm 22 in such a way as to bring the cutting element 24 to perform a substantially complete circular path of 360° or an angular portion thereof.

In the preferred embodiment of the Figures, said rack 40 is slidingly arranged with respect to said base 30 and configured to engage with two pinion gears 25 arranged along their rotation axis, and fixed respect to two arms 22, in such a way that each arm 22 is configured to bring the respective cutting element 24 to perform an angular movement about the rotation axis of the arm 22.

Figures 2A, 2B:
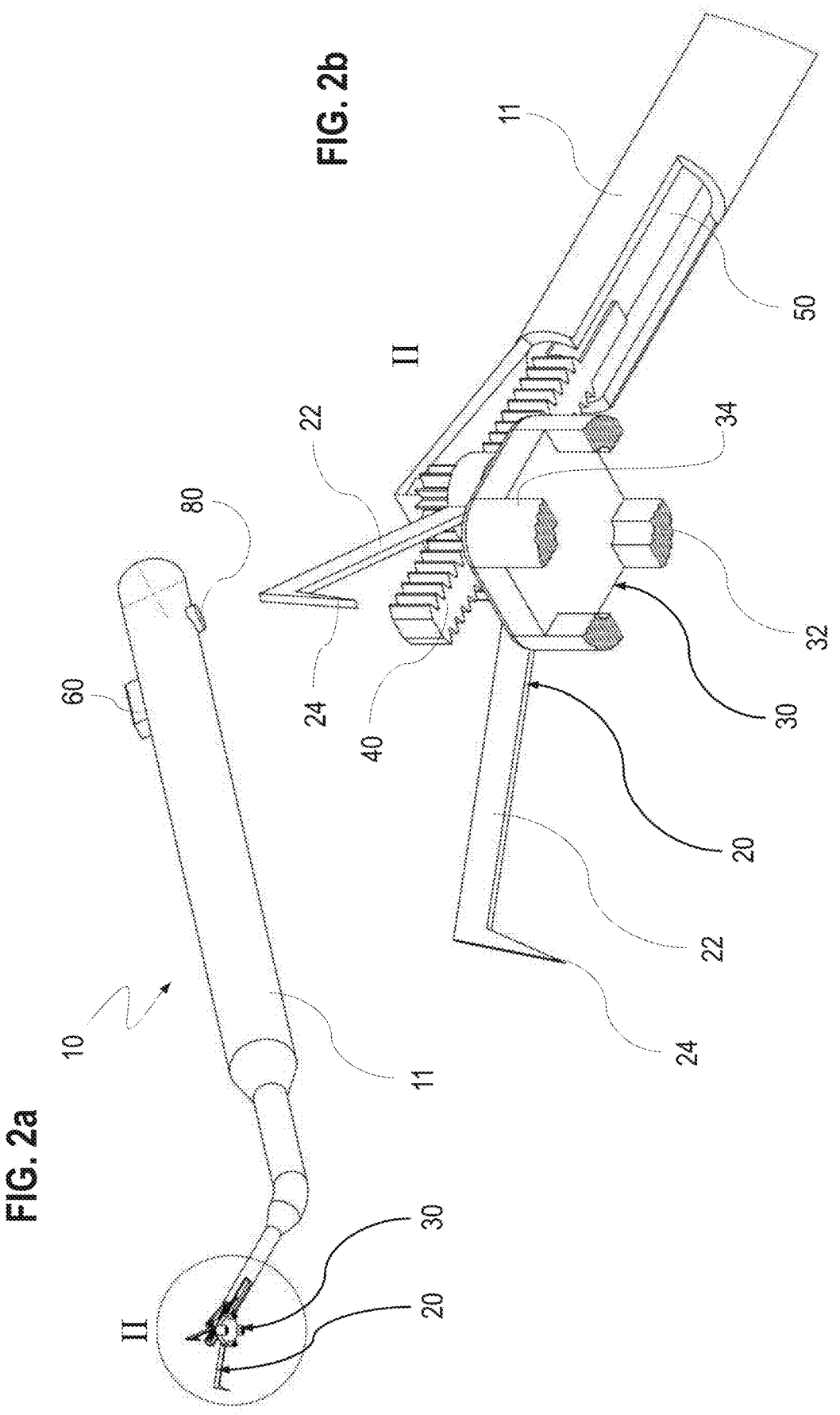
Figures 3A, 3B:
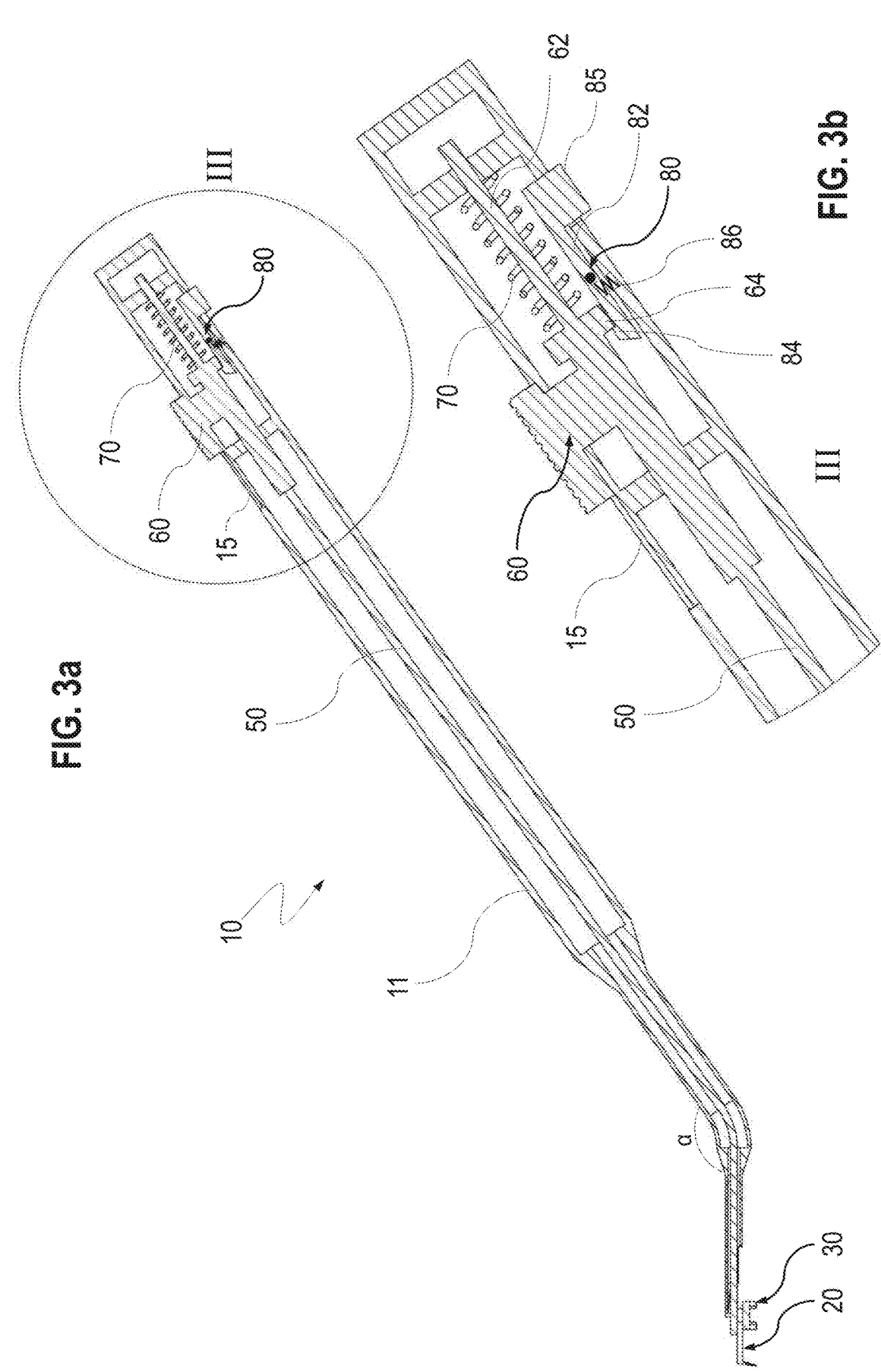
FIG. 3*a* is a schematic representation of a longitudinal sectional view of the same preferred form of embodiment of the same ophthalmological surgical instrument that is the subject matter of the present invention.
FIG. 3*b* is a schematic partial cross-sectional representation of a detail view of FIG. 3*a;*

With particular reference also to FIGS. 2*b*, 3*a*, 3*b*, said rack 40 is advantageously connected to a flexible rod 50 internally arranged to said body 11. Said flexible rod 50 is slidingly operable by means of a slider 60 slidingly disposed in an opening 15 formed on said body 11, said slider 60 being suitable for being manually operated by the fingers of a user.

The slider 60 also comprises a first elastic element 70, suitable for returning the slider 60 and the rod 50 to an initial stable position corresponding to a limit configuration of the arms 22 and respective cutting elements 24.

Figures 4A, 4B, 4C, 4D:
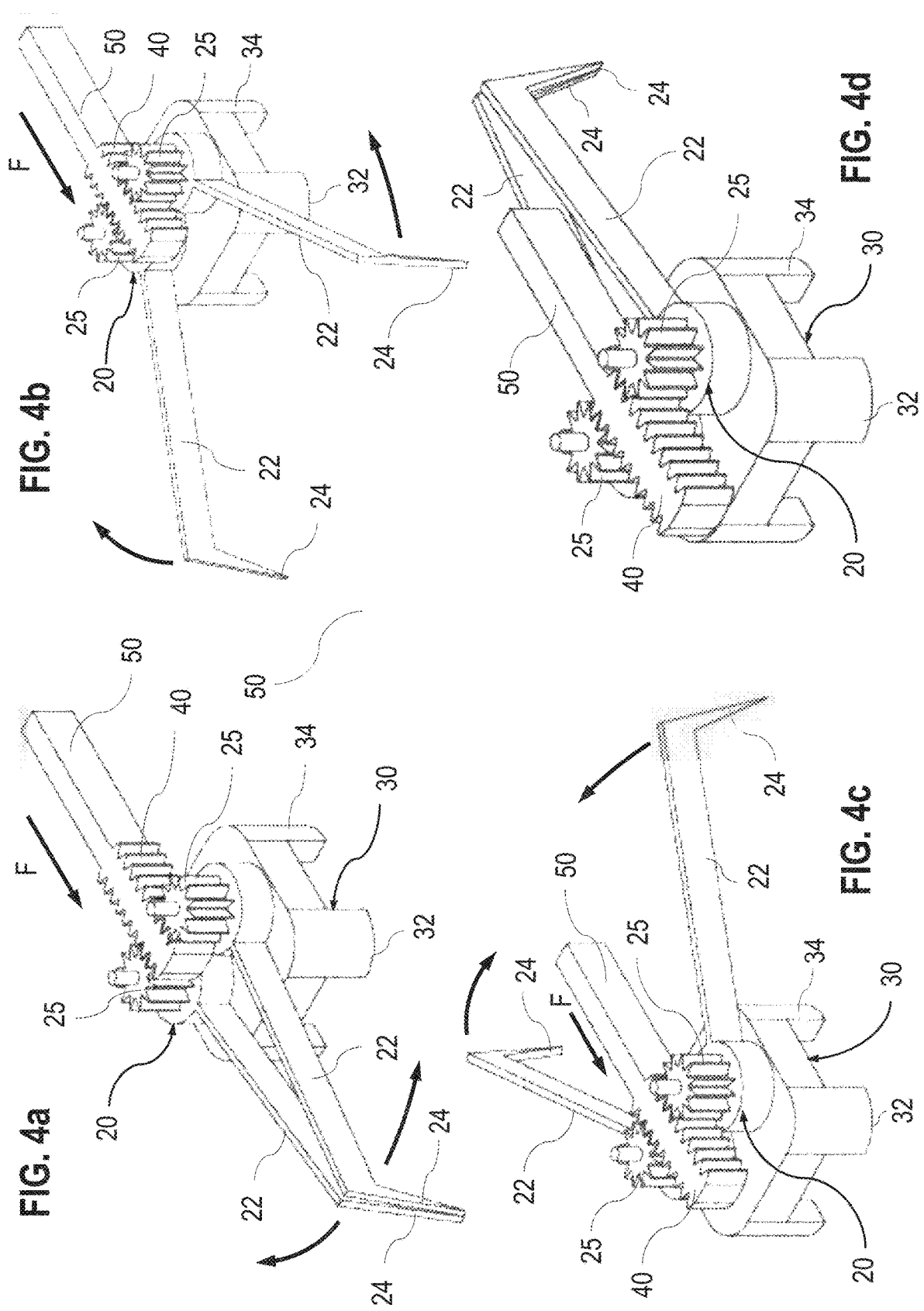
FIGS. 4*a* to 4*d* are a schematic representations, in axonometric and partial perspective view, of the cutting edge handling mechanism according to the preferred embodiment of the ophthalmological surgical instrument that subject matter of the present invention, starting from a limit configuration of FIG. 4*a* to a limit configuration of FIG. 4*d*, passing through intermediate configurations of FIGS. 4*b* and 4*c;*

Still with reference to the same figures, said slider 60 can also be placed in cooperation with a retaining element 80 configured to engaging and maintaining the slider and the rod 50 stationary in a position with the elastic element 70 loaded, corresponding to a limit configuration equal to the initial limit configuration of the arms 22 and respective cutting elements 24 of FIG. 4*a*.

With particular reference to FIGS. 3*a* and 3*b*, the elastic element 70 can also be advantageously arranged coaxially to a guide rod 62.

The acceleration of the cutting edges 24 under the action of the elastic element 70 is damped during the capsulorhexis phase by the deformation and friction of the rod 50 in the body 11. In an alternative embodiment of the surgical instrument 10, with particular reference also to FIGS. 6*a* and 6*b*, the slider 60 and the elastic element 70 can also be placed in cooperation with an optional damper 90 arranged in series or in parallel with the same elastic element 70, said damper being configured for limiting the translation speed of the rod 50 and rack 40 by the releasing action of the elastic force of the elastic element, so as to transfer to the cutting elements 24 of the arms 22, through the rack 40 and pinion gears 25, a slow constant and uniform motion.

Said damper 90 may include a conventional friction damper or dissipator also of the viscous type, arranged in series and in parallel with the elastic element 70.

Figures 6A, 6B:
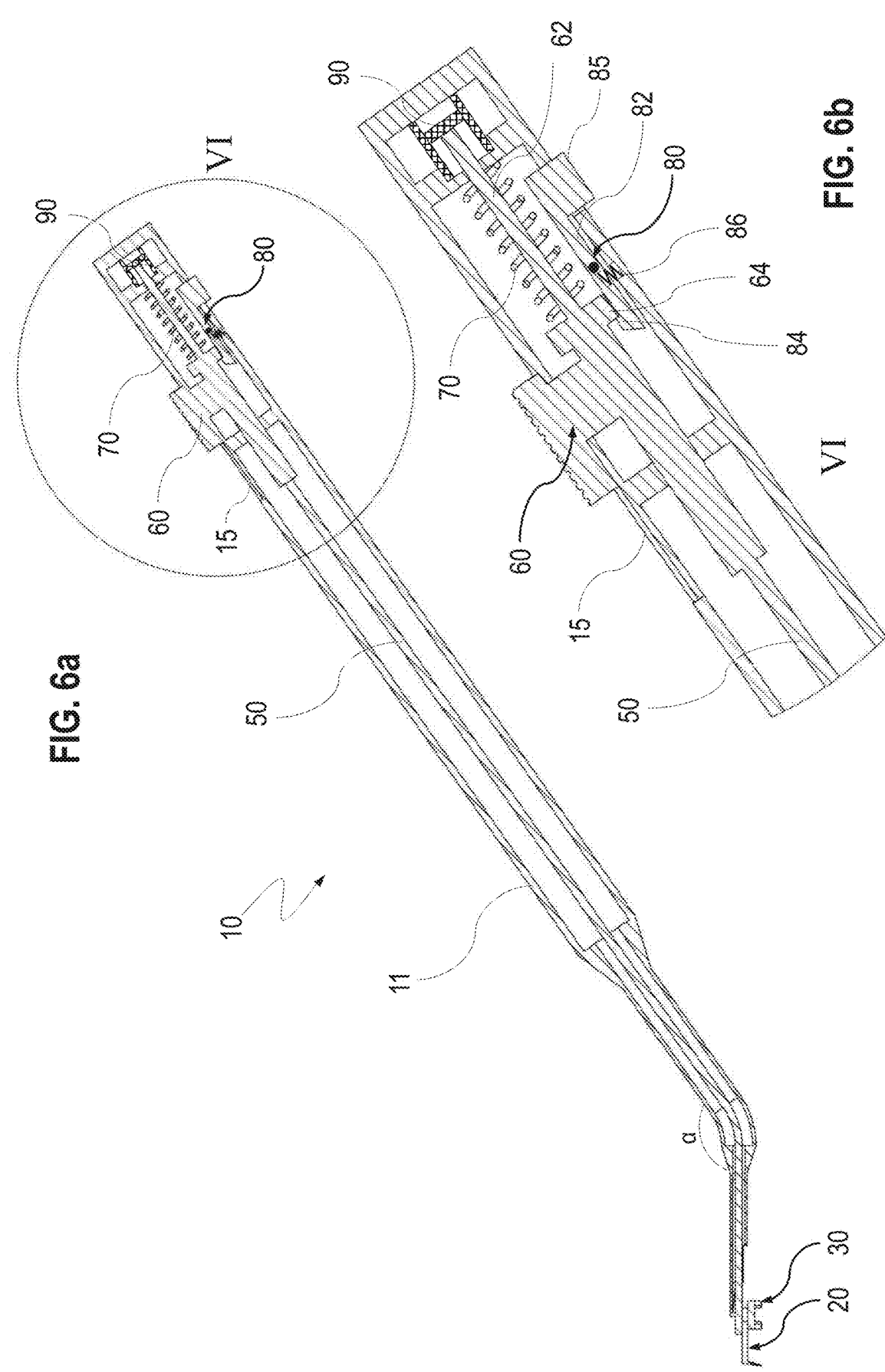
FIG. 6*a* is a schematic representation of a longitudinal sectional view of an alternative variant embodiment of the ophthalmological surgical instrument subject matter of the present invention provided with a damping element.
FIG. 6*b* is a schematic partial cross-sectional representation of a detail view of FIG. 6*a;*

In the variant embodiment of FIG. 6*b*, said damper 90 is integrally arranged with respect to the body 11 and it is connected in motion with the guide rod 62 integrally arranged with the slider 60. In an alternative embodiment said damper 90 may also be integrally arranged in the slider 60 and connected with guide rod 62 that, in this case, is integrally arranged with the body 11.

With particular reference to the detail of FIG. 3*b*, in a preferred embodiment given for illustrative and non-limiting purposes only, said retaining element 80 comprises a ratchet-like mechanism comprising a pawl 82 hinged with respect to the body 11 and provided to one of its end with a first catch 84 capable of engaging the slider 60 and keeping it locked in position at a second catch 64 when the same is in a rearward position with the first elastic element 70 loaded. Said pawl 82 is provided on its opposite end with a drive portion 85 arranged so as to extend externally to the body 11 through an opening made in the same body, said drive portion 85 being suitable for be operated by the medical user in such a way as to lead the pawl 82 in a rotation so as to disengage the first catch 84 from the second catch 64 of the slider 60 in order to free the same slider 60 and allow it to translate together with the rod 50 with respect to the body 11.

Said retaining element 80 is also provided with a second elastic element 86 suitable for keeping the pawl 82 stationary in a locked position with the first catch 84 engaging the second catch 64 of the slider 60, as shown in FIG. 3*b*.

With particular reference to FIG. 3*a*, the body 11 of said surgical instrument 10 can be bent by a generic angle α at an intermediate portion between the two ends in such a way that it can be more easily gripped by the user, preferably, for a surgical instrument for use in ophthalmology, said angle α is between 110° and 150°.

Body 11 and cutting assembly 20 are generally made of materials suitable for surgical instrument construction, metal alloys or even polymeric plastic materials, they can also be made by material sintering or additive manufacturing processes.

The arms 22 and cutting elements 24 are preferably made of surgical instrument material and metal alloys and can advantageously be separable and interchangeable disposable for a single-use.

Figure 5:
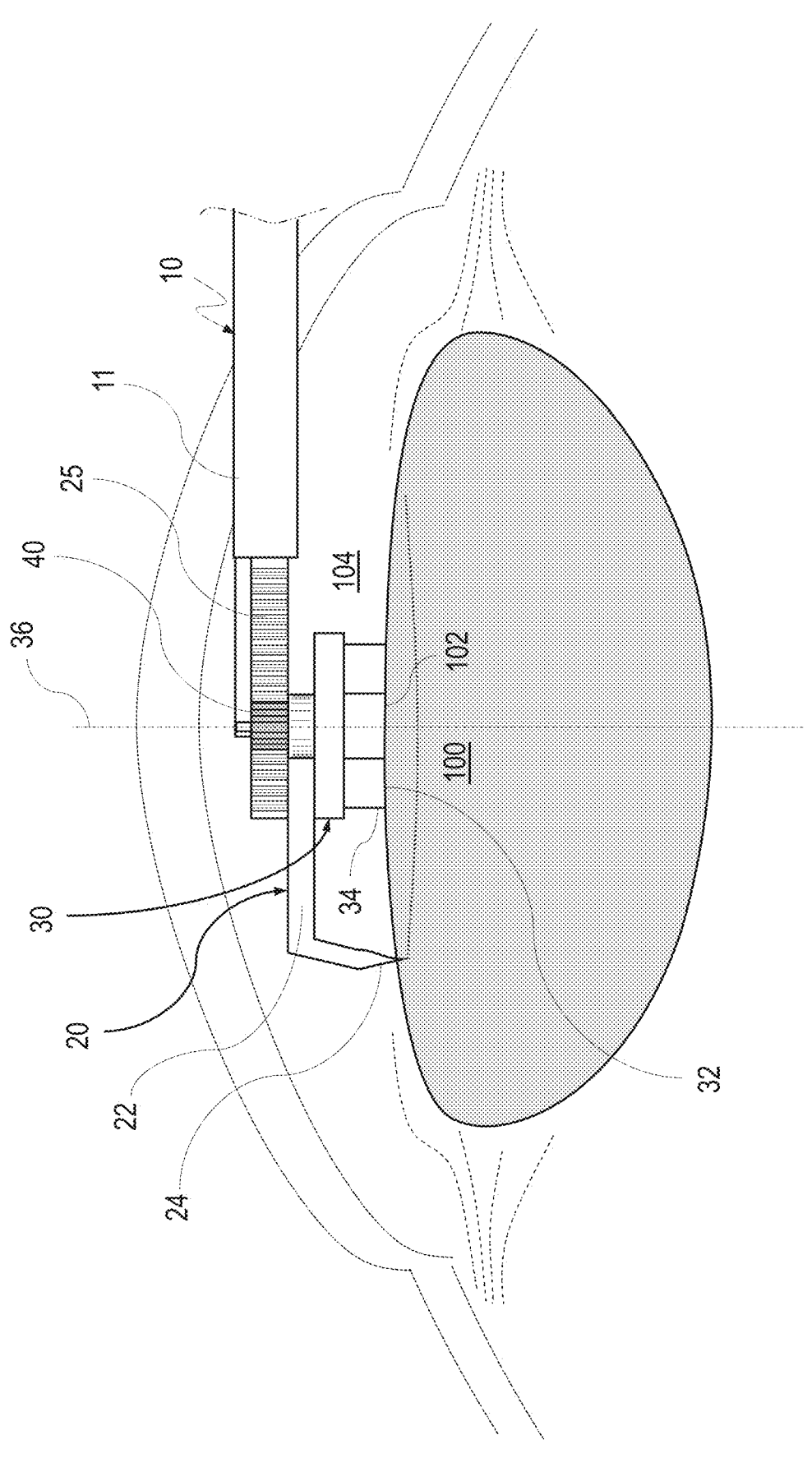
FIG. 5 is a schematic representation of a side and partial view of the ophthalmological surgical instrument subject matter of the present invention in the operational use, arranged with the cutting edges on the anterior surface of an eye capsule containing the crystalline lens.

With particular reference also to FIG. 5, the cutting elements 24 can also be dimensioned and formed in series having different shapes and different sizes so as to be suitable for perform more or less deep and angled incisions on the anterior outer surface 102 of the capsule 100. Said arms 22 or cutting edges 24 can also be advantageously bent or oriented in such a way to positioning on the anterior outer surface 102 of the capsule 100 in a direction substantially perpendicular or normal thereto.

With particular reference to FIG. 2b and FIG. 5, again in the preferred embodiment form of the surgical instrument 10, the base 30 of the cutting assembly 20 can advantageously be shaped so as to match and conjugate with the anterior outer surface 102 in order to be stably rested on the outer tissue of the capsule 100.

Said base 30 can have a support surface 32, preferably having a convex conformation and conjugate with said front outer surface 102 of the capsule 100, having an symmetry axis 36 substantially located between the translation axis of the rack 4 and the axis joining the centers of rotation of the two arms 22, or a partial support surface 32 comprising a plurality of feet 34 in such a way to provide a stable support on the front outer surface 102 of the capsule 100.

In an alternative embodiment, not shown, wherein the surgical instrument 10 comprises a single cutting edge provided with a single arm 22, said symmetry axis 36 substantially coincides with the axis of rotation of the arm 22 itself.

Said support surface 32, whether uniform or subdivided into a plurality of portions formed on said feet 34, can advantageously be provided with a rough or knurled surface or a surface coated with a layer of adherent material, suitable for improving its coefficient of friction with the front outer surface 102 and preventing unintentional sliding of the surgical instrument 10.

From the description of the ophthalmic surgical instrument 10 subject matter of the present invention, its operation described below is evident.

With reference to the figures, particularly FIGS. 4a to 4d, the surgical instrument 10 subject matter of the present invention is particularly advantageous because it allows the medical user to be able to make a partially developed or full 360° incision, of the anterior outer surface 102 of the capsule 100 containing the crystalline lens, in a precise, symmetrical manner and of the desired depth.

With reference again to the preferred embodiments of the figures, particularly FIGS. 2a, 3b and 5, the surgeon can hold and support the surgical instrument 10 by the oblong part 11 and operate the slider 60 by translating toward the end of the body 11 opposite the cutting elements 24. In this way, the slider 60 can arm the cutting elements 20 by translating the rod 50 and rack 40 until the arms 22 with their respective cutting elements 24 are brought into the limit configuration of FIG. 4a and loading the elastic element 70 with potential elastic energy. This translation movement of the slider 60 together with the rod 50 results in compression of the elastic element 70 until the pawl 82 of the retaining element 80 engages the first catch 84 and the second catch 64 under the action of the second elastic element 86 in such a way as to keep the slider 60, rod 50 and rack 40 in the backward position and bring the arms 22 from the limit configuration of FIG. 4d to the limit configuration of FIG. 4a with the surgical instrument 10 armed. The retaining element 80 engages the slider 60 preventing the elastic element 70 from returning it to the resting position with the rod 50 and the cutter assembly in the opposite configuration. At the same time by means of rod 62 it can also be possible to operate on an optional damper 90, for example, the plunger of a viscous damper, as shown in the alternative embodiment form in FIG. 6b.

With particular reference to FIG. 5, once the surgical instrument 10 has been armed, the surgeon can position the instrument in the anterior chamber 104 through the lateral incisions or accesses with the support surface 32 or the feet 34 of the base 30 at the anterior outer surface 102 of the capsule 100 containing the crystalline lens to be surgically treated, centring it with respect to the same crystalline lens in the patient's eye prior to the capsulorhexis phase. The support surface 32 can also advantageously have a conformation such that it fits and centers with the shape of the anterior outer surface 102 of the capsule 100 containing the crystalline lens.

When the cutting assembly 20 in the configuration of FIG. 4a is stably arranged on the anterior outer surface 102 the juxtaposed cutting elements 24 penetrate the outer tissue of the capsule 100 to a desired depth by making a preliminary incision of the tissue.

Still with reference to FIG. 5, once the surgical instrument 10 is stably positioned on the anterior outer surface 102 of the patient's capsule 100, with the cutting elements 24 in the preliminary incision position, the surgeon acts on the retaining element 80 by releasing the elastic element 70, which by extending causes the slider 60 and rod 50 to translate in the direction of the cutting element assembly 20.

The rod 50 pushes the rack 40 integral with it to engage with the pinion gears 25 thus bringing the arms 22 to perform together with the cutting elements 24, a circular or semi-circular movement from the limiting configuration of FIG. 4a to the limiting configuration of FIG. 4d, bringing the elastic element 70 to the resting position, passing through the generic limiting configurations of FIGS. 4b and 4c, thus accomplishing in a single step the capsulorhexis phase with the essentially circular 360° incision or a desired angular portion of the capsule containing the crystalline lens.

The presence of a possible damper 90, in a possible alternative variant embodiment of FIG. 6b, allows the elastic element 70 to slowly and steadily release its energy in such a way as to prevent abrupt snaps and accelerations that would be transmitted to the arms 22 and cutting elements 24 through the slider 60 the rod 50 and the rack that engages kinematically the pinion gears 25. This allows the surgeon to easily control the correct path of the cutting elements 24 and the depth of the incision as the arms 22 rotate. The internal friction of the rod 50 in the body 11 and the arms 22 and the friction of the cutting elements 24 with the tissues of the eye and the medical fluids or gels preliminarily injected into the anterior chamber 104 is generally sufficient to ensure adequate damping of the energy of the elastic element 70 and to restrain the abrupt movement of the cutting elements 24.

From the description of the ophthalmic surgical instrument 10 subject matter of the present invention the advantages described below are obvious.

The ophthalmological surgical instrument 10 subject matter of the present invention is particularly advantageous because it allows even unskilled and inexperienced surgeons to perform a precise and safe capsulorhexis phase, thus guaranteeing a better success of the surgery and in a shorter time.

Another further advantage of surgical instrument 10 is that it can provide the user with a tool with disposable and interchangeable cutting edges that can be selected according to the anatomy of the patient's eye and the desired incision depth.

Although the invention has been described above with particular reference to a preferred embodiment, given for illustrative and non-limiting purposes, numerous modifications and variations will become apparent to a person skilled in the art in light of the above description.

The present invention, therefore, is intended to encompass all modifications and variations falling within the scope of protection of the following claims.

The invention claimed is:

1. An ophthalmological surgical instrument comprising:
a hollow body having an oblong shape and a portion shaped to function as a handle; and
a cutting assembly positioned on an end of the hollow body and comprising at least one arm connected to the hollow body and including at least one cutting element;
wherein the at least one arm is pivotally hinged to a base fixed to the hollow body;
wherein the at least one arm is configured rotatively cooperate with a toothed rack that is slidingly positionable with respect to the base; and
wherein the at least one arm is further connected to at least one conjugate pinion gear that is positioned along a rotation axis and rotatively moveable with the at least one arm along the rotation axis relative to the base;
wherein the toothed rack is manually operable to be slidingly moved by a user;
wherein one of the at least one arms is separable from the hollow body and interchangeable with another of the at least one arms; and
wherein the at least one cutting element is separable from the at least one arm and interchangeable with another at least one respective cutting element.

2. The surgical instrument according to claim 1, wherein slidably moving the toothed rack causes a corresponding rotative movement of the at least one arm and the at least one cutting element to perform a substantially circular path of up to 360° relative to the base.

3. The surgical instrument according to claim 2, wherein the cutting assembly comprises two arms each having a respective cutting element; and wherein each of the two arms are configured to rotatively move relative to the base in a semi-circular path.

4. The surgical instrument according to claim 1, wherein the toothed rack is connected to a flexible rod that is positioned within the hollow body; and wherein the flexible rod is slidingly positionable relative to the hollow body and operable to slidably move in conjunction with a slider that is slidingly positioned in an opening that is formed on the hollow body.

5. The surgical instrument according to claim 4, wherein the slider comprises an elastic element operable to return the slider and the flexible rod to a first rotation limit position of the at least one arm.

6. The surgical instrument according to claim 5, wherein the slider is positioned to cooperate with a retaining element that maintains the slider and the flexible rod in a stationary position and the elastic element in a loaded position corresponding to a second rotation limit position that is opposite to the first rotation limit position of the at least one arm.

7. The surgical instrument according to claim 5, wherein the elastic element is positioned to cooperate with a damper that is at least one of positioned in series with the elastic element and positioned in parallel with the elastic element.

8. The surgical instrument according to claim 6, wherein the retaining element comprises a pawl that is hinged with respect to the hollow body; wherein the pawl includes a first end that comprises a first catch that is engageable with a second catch of the slider via a second elastic element; wherein the pawl includes a second end that is opposite the first end and comprises a drive portion.

9. The surgical instrument according to claim 1, wherein the hollow body is bendable at an intermediate portion thereof by an angle alpha ($\alpha$).

10. The surgical instrument according to claim 1, wherein the hollow body and the cutting assembly comprise at least one of metal alloy, polymeric plastic material, sintered material, and additive manufactured material.

11. The surgical instrument according to claim 1, wherein the at least one arm and the at least one cutting element each respectively comprise at least one shape and size chosen from a series consisting of a plurality of differing shapes and sizes.

12. The surgical instrument according to claim 1, wherein the base of the cutting assembly comprises a support surface having a convex formation that is substantially paraboloid shaped.

13. The surgical instrument according to claim 1, wherein the base of the cutting assembly comprises a partial support surface that includes a plurality of feet positioned to provide for stable friction when positioned on surfaces of eyes.

14. The surgical instrument according to claim 13, wherein the support surface and the plurality of feet include at least one of a rough surface and a knurled surface.

* * * * *